United States Patent [19]
Rosengart et al.

[11] Patent Number: 5,997,509
[45] Date of Patent: Dec. 7, 1999

[54] MINIMALLY INVASIVE GENE THERAPY DELIVERY DEVICE AND METHOD

[75] Inventors: Todd K. Rosengart, Tenafly, N.J.; Ronald G. Crystal, Potomac, Md.; Raymond A. Hartman, Carlsbad, Calif.

[73] Assignee: Cornell Research Foundation, Inc., Ithaca, N.Y.

[21] Appl. No.: 09/035,892

[22] Filed: Mar. 6, 1998

[51] Int. Cl.⁶ .......................... A61M 5/178; A61M 5/00
[52] U.S. Cl. .................... 604/164; 604/116; 604/181; 604/187
[58] Field of Search ................. 604/1, 95, 115, 604/116, 117, 181, 188, 187, 164, 207, 208, 211, 218, 246, 264, 272

[56] References Cited

U.S. PATENT DOCUMENTS

| | | |
|---|---|---|
| 2,498,692 | 2/1950 | Mains . |
| 2,688,329 | 9/1954 | Wallace . |
| 2,700,385 | 1/1955 | Ortiz . |
| 3,797,491 | 3/1974 | Hurschman ............................ 128/218 |
| 4,222,380 | 9/1980 | Terayama . |
| 4,243,035 | 1/1981 | Barrett ................................... 128/215 |
| 4,578,061 | 3/1986 | Lemelson . |
| 4,787,891 | 11/1988 | Levin et al. ............................ 604/136 |
| 4,838,854 | 6/1989 | Kuzmanovich . |
| 4,861,336 | 8/1989 | Helzel . |
| 4,946,442 | 8/1990 | Sanagi . |
| 4,976,688 | 12/1990 | Rosenblum . |
| 4,994,041 | 2/1991 | Dombrowski et al. ................. 604/164 |
| 5,147,307 | 9/1992 | Gluck ..................................... 604/116 |
| 5,192,270 | 3/1993 | Carswell, Jr. .......................... 604/116 |
| 5,261,889 | 11/1993 | Laine et al. . |
| 5,269,754 | 12/1993 | Rydell . |
| 5,322,510 | 6/1994 | Lindner et al. . |
| 5,354,279 | 10/1994 | Höfling . |
| 5,380,292 | 1/1995 | Wilson . |
| 5,417,662 | 5/1995 | Hjertman et al. ...................... 604/117 |
| 5,441,499 | 8/1995 | Fritzsch . |
| 5,464,395 | 11/1995 | Faxon et al. . |
| 5,522,815 | 6/1996 | Durgin, Jr. et al. . |
| 5,536,251 | 7/1996 | Evard et al. . |
| 5,567,217 | 10/1996 | Luther ..................................... 604/280 |
| 5,569,237 | 10/1996 | Beckenstein .............................. 606/1 |
| 5,674,197 | 10/1997 | Van Muiden et al. .................... 604/95 |
| 5,820,592 | 10/1998 | Hammerslag ............................. 604/95 |
| 5,827,216 | 10/1998 | Igo et al. ................................. 604/21 |
| 5,845,646 | 12/1998 | Lemelson ................................ 128/899 |

*Primary Examiner*—Ronald K. Stright, Jr.
*Assistant Examiner*—Patricia Bianco
*Attorney, Agent, or Firm*—Leydig, Voit & Mayer, Ltd.

[57] ABSTRACT

The invention is directed to a device and method for delivering a therapeutic substance to a bodily tissue in a minimally invasive manner. The device includes an elongate flexible tubular member having a proximal end and a distal end. A control means is provided for enabling the distal end of the tubular member to be controllably flexed in a transverse manner for positioning the distal end of the tubular member proximate to the bodily tissue to be treated. A hollow needle is disposed at the distal end of the tubular member for delivering the therapeutic substance into the bodily tissue. A marking means is also included for indicating when a injection has been made in the tissue. The invention is particularly useful for treatment of ischemic heart disease by gene therapy.

20 Claims, 3 Drawing Sheets

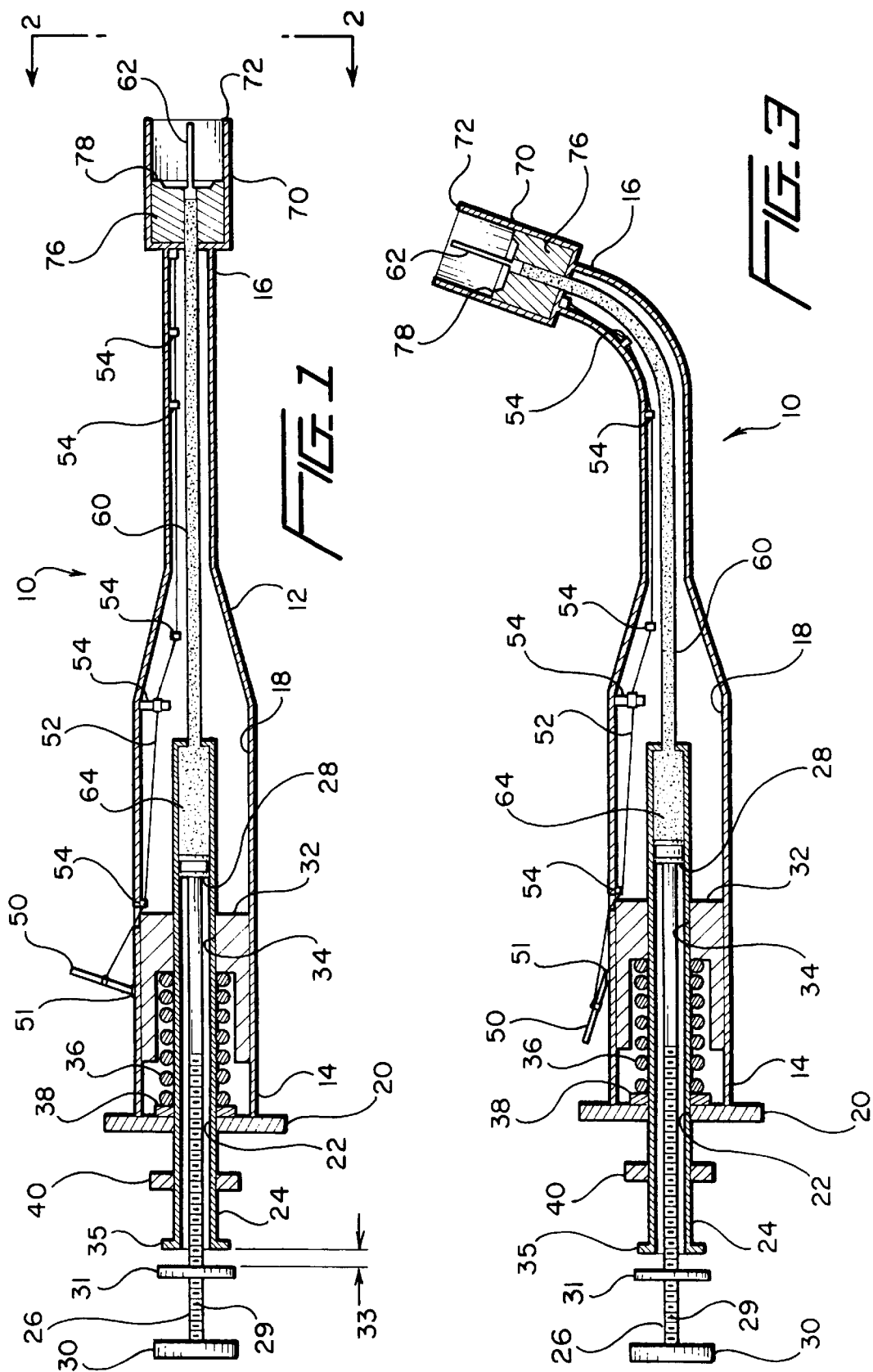

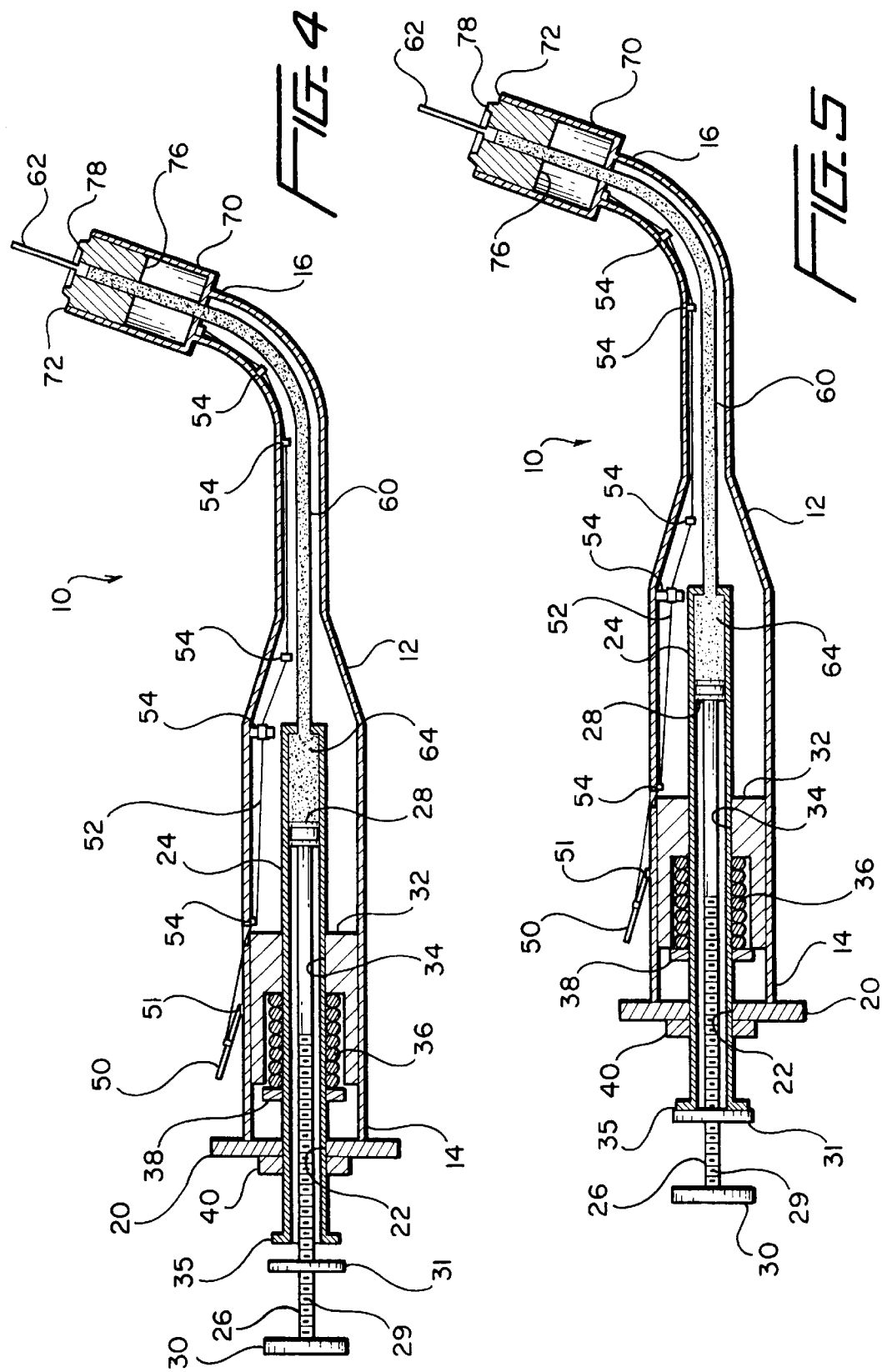

MINIMALLY INVASIVE GENE THERAPY DELIVERY DEVICE AND METHOD

FIELD OF THE INVENTION

This invention embodies a therapeutic medical device and a method of treatment. In particular, the device is suitable for treating target tissue of a patient by injection of predetermined quantities of a substance into bodily tissue at successive locations within the patient's body. One particular application to which this invention may be applied is the delivery of therapeutic substances to the heart to induce angiogenesis for improving blood flow in heart tissue.

DESCRIPTION OF THE PRIOR ART

Despite the recent advances in the treatment of ischemic heart disease, there still exist a significant number of patients for whom conventional therapies such as angioplasty and coronary bypass surgery are not feasible options. In particular, alternative therapies are required for patients in a number of circumstances. For example, patients with diffuse small vessel coronary artery disease can not be treated by conventional coronary bypass surgery because of the small size and large number of diseased vessel segments. In other patients, re-occlusion of a diseased vessel may occur despite multiple angioplastic procedures or bypass surgeries. Accordingly, the need exists for alternative intervention methods.

One promising alternative treatment for ischemic heart disease is the delivery of angiogenesis-promoting substances to the heart tissue to induce angiogenesis. Angiogenesis is a complex biological process that results in the growth of new blood vessels within tissue. Angiogenesis is an essential process common to several normal and pathologic conditions including embryologic development, wound healing, development of neoplasms, and the like.

Angiogenesis has also been induced in heart tissue for reperfusion of tissue compromised by myocardial ischemia. Several growth factors have been identified and are intimately involved in initiating and promoting angiogenesis in tissue within a living body. These growth factors are typically proteins which stimulate endothelial cell reproduction in the target tissue. The tissue must be exposed to the growth factors for a period of time, i.e., a number of days. In addition, the growth factor should be limited to the target tissue so that angiogenesis is not induced in sensitive non-diseased organs, such as the retina, or in occult tumors.

The growth factor may be delivered to the target tissue through the use of indwelling catheters over a period of time. However, a preferred method of delivering the growth factor is in the form of gene transfer by a replication deficient adenoviral vector. Under this method, a quantity of adenovirus having the desired genetic component is delivered to the treatment area by injection in solution.

In the past, an open-chest procedure has been used to deliver the treatment solution. According to this procedure, the patient's chest is opened surgically to expose the heart. The solution containing the adenovirus is then delivered to the heart tissue by using a syringe to make a number of injections in a grid-like pattern, with the surgeon keeping track of the location of each injection. Once injected, the adenovirus causes the cells in the target tissue to express the desired growth factor protein, and this protein expression from the treated cells will continue for the desired period of time. Previous studies have shown the feasibility and efficacy of safe, sustained, and localized expression of angiogenesis-promoting growth factors utilizing adenoviral-mediated gene transfer therapy.

It is desirable, however, to be able to provide the above-described therapy without the necessity of performing open-chest surgery on the patient. Accordingly, the present invention sets forth an apparatus and method for providing gene therapy treatment to the heart or other internal organs in a minimally invasive manner. The present invention also provides an apparatus and method for delivering angiogenesis-promoting substances to an area of diseased tissue with greater ease and efficiency, and with reduced trauma and recovery time for the patient. Accordingly, the subject invention could be potentially helpful to hundreds of thousands of patients with severe ischemic heart disease who are not candidates for surgical bypass or balloon angioplasty.

SUMMARY OF THE INVENTION

The present invention embodies a novel, minimally invasive injection apparatus and method. The invention is useful, for example, in gene transfer therapy for injecting an angiogenesis-promoting factor into living tissue, such as into the myocardium. The injection device includes an elongate flexible tubular body having a proximal end and a distal end. A hollow needle is mounted on the distal end of the tubular body. The needle is capable of penetrating the target tissue for delivering a therapeutic substance to the tissue.

In addition, a marking means is mounted on a platen on the distal end of the tubular member. When the therapeutic substance is delivered to the bodily tissue, the marking means leaves a discernable mark on the target tissue so that the surgeon may keep track of which areas of tissue have been treated by viewing through an endoscope, or by other means. The platen and needle are fixed relative to each other so that the platen, by contacting the tissue surface, ensures that the needle penetrates the target tissue to the same depth with each injection.

A control means may also be included with the device for controllably positioning the distal end of the tubular member to facilitate proper positioning and insertion of the needle. Furthermore, a metering means may also be included for controlling the amount of therapeutic substance injected at each successive injection site.

Under the method of the invention, a therapeutic substance may be injected into living tissue successively at a plurality of locations inside the body in a minimally invasive manner. The injections may be made for a variety of purposes in a variety of bodily tissues. However, the present invention is especially suitable for delivering gene therapy to the heart. In particular, an angiogenesis-promoting factor may be introduced into myocardial territories in predetermined quantities at a plurality of points to induce the growth of bypass vessels which may allow the bridging of narrowed or occluded coronary vessels. The treatment may also be used to induce the growth of new vessels in myocardial territories poorly supplied by the native coronary vasculature. The treatment method may also be used to deliver therapeutic substances to other bodily tissues in a minimally invasive manner.

BRIEF DESCRIPTION OF THE DRAWINGS

FIG. 1 is an enlarged cross section elevation view of the delivery device of the present invention.

FIG. 3 shows the delivery device of FIG. 1 with the distal portion flexed transversely.

FIG. 4 shows the delivery device of FIG. 3 with the needle and marking platen extended.

FIG. 5 shows the delivery device of FIG. 4 following injection of a portion of the therapeutic substance.

DESCRIPTION OF THE PREFERRED EMBODIMENT

Figure 2:
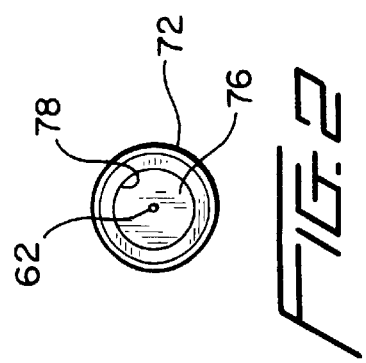
FIG. 2 shows an end view of the device of FIG. 1 as taken along line 2—2.

The invention is directed to a method and apparatus for delivering therapeutic treatment to body tissues. The apparatus includes a delivery device 10, as illustrated in FIGS. 1 and 2, capable of injecting a therapeutic substance into bodily tissue through a minimally invasive method. Device 10 may be inserted through a thoracoscopic port (not shown), giving thoracoscopic access to the patient's heart or other tissue. The device may advantageously be used to inject a substance in a grid-like or other pattern so that by making successive injections of a predetermined quantity of substance having a predictable diffusion mobility, an entire area of tissue can be treated.

Delivery device 10 includes an elongate flexible tubular member 12 having a proximal end 14 and a distal end 16. Tubular member 12 is constructed of a flexible material such as polyurethane, polyvinyl chloride, polyethylene, or other suitable flexible biocompatible materials. Tubular member 12 includes a lumen 18 which passes from proximal end 14 to distal end 16, and which has a generally circular cross section. A cap 20 is mounted on the proximal end 14 of tubular member 12, and includes a circular hole 22 to allow passage of a syringe 24. Syringe 24 includes a cylindrical body having a plunger shaft 26 and a plunger 28 slidably mounted therein. Plunger 28 is mounted on the distal end of plunger shaft 26, and a plunger thumb button 30 is mounted on the proximal end of plunger shaft 26.

Plunger shaft 26 may include screw threads or other gradations 29 formed along its length. A plunger stop 31 is movably mounted on plunger shaft 26 and positionable at a predetermined distance 33 from the proximal end 35 of syringe 24. Plunger stop 31 ensures that when plunger 28 is depressed, only a predetermined amount of therapeutic substance is dispensed from syringe 24. Following delivery of the substance, plunger stop 31 is reset by moving proximally back along plunger shaft 26 the predetermined distance 33. This may be accomplished by turning plunger stop 31 back along threads 29 or the like. Syringe 24 is thereby set to deliver the next predetermined dose of therapeutic substance at the next injection location. Other means for metering the amount of therapeutic substance delivered may also be used. For example, a ratchet mechanism (not shown) may be incorporated into the syringe for enabling consistent delivery of successive constant amounts of therapeutic substance in an aliquot manner. The physician depresses plunger button 30 until the ratchet mechanism stops the forward motion at a predetermined distance. The ratchet mechanism would then reset to enable to the plunger to be depressed an additional predetermined distance, and so forth.

A cylindrical support 32 is located within lumen 18 of tubular member 12. Cylindrical support 32 has a circular opening 34 therethrough for receiving and supporting syringe 24. Syringe 24 is able to slide axially within circular hole 22 in cap 20 and circular opening 34 in cylindrical support 32. A spring 36 is fixedly mounted concentrically on syringe 24 between cylindrical support 32 and an annular spring stop 38. Spring stop 38 is a disk-shaped member mounted on syringe 24, and is fixed to syringe 24 so that it moves axially as syringe 24 is moved axially. A second stop member 40 is fixedly mounted on syringe 24 proximal of cap 20. Second stop member 40 is also a disk-shaped member which is fixed to the exterior of syringe 24. Second stop member 40 prevents syringe 24 from being advanced too far into tubular body 12, when syringe 24 is moved axially in the distal direction relative to tubular body 12.

A control lever 50 is mounted on the side of tubular body 12 for controlling the position of distal end 16 of tubular body 12. Control lever 50 is pivotally mounted to tubular body 12 at pivot point 51, and is connected to a control wire 52 which is connected to the distal end 16 of tubular body 12 in an offset manner. Control wire 52 may be retained within eyelets 54 located within lumen 18 of tubular body 12, or may be retained within a separate lumen (not shown), or by other means, as is known in the art.

As illustrated in FIG. 3, when control lever 50 is pulled in the proximal direction, it may be seen that control wire 52 will pull on the distal end 16 of tubular body 12. This causes tubular body 12 to bend or flex transversely so that distal end 16 is disposed in an oblique direction relative to the major axis of tubular body 12. An adjustment mechanism (not shown) may be included for holding control lever 50 in a particular desired position. In addition, other control devices may be substituted for lever 50, as is known in the art. For example, a threaded knob (not shown) may be used in place of lever 50, with the knob being turned in one direction to pull on control wire 52, and being turned in the other direction to release tension on control wire 52.

A flexible tube 60 is connected to the distal end of syringe 24, in fluid communication with syringe 24. The distal end of flexible tube 60 is connected to a hollow needle 62 of the hypodermic type. A therapeutic substance 64 contained within syringe 24 may be expelled through needle 62 by pressing syringe plunger button 30. This forces the therapeutic substance from syringe 24, through flexible tube 60, and out the distal end of needle 62.

To prevent needle 62 from accidentally penetrating non-target tissue during positioning of device 10, a cup 70 is mounted on the distal end 16 of tubular body 12 to serve as a guard. Cup 70 is a hollow cylindrical member, and includes a wall having a distal edge 72 which extends at least as far as the tip of needle 62 when needle 62 is in the retracted position, as illustrated in FIGS. 1 and 3. Accordingly, as long as needle 62 is retracted, cup 70 will prevent needle 62 from contacting non-target areas during placement of device 10 within a patient.

Figure 6:
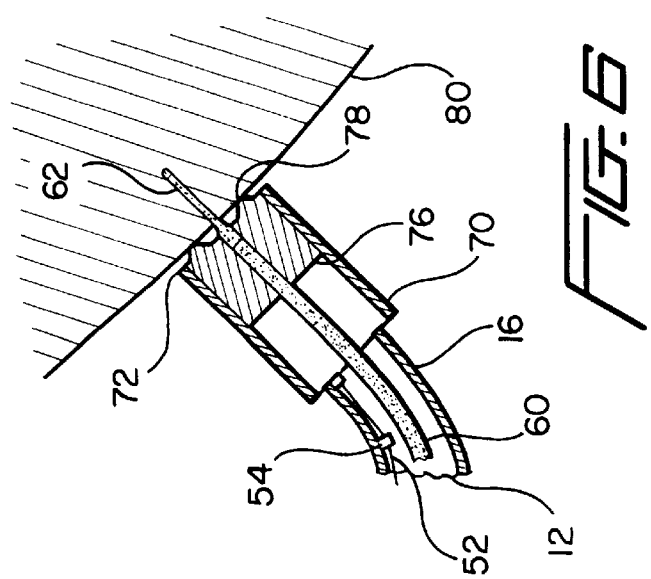
FIG. 6 shows the delivery device of FIGS. 5 during injection of the therapeutic substance into tissue.

A cylindrical platen 76 is located within cup 70, and is connected to flexible tube 60 and needle 62. Platen 76 moves forward within cup 70 as needle 62 is extended. Because needle 62 and platen 76 are fixed relative to each other, when needle 62 is inserted into target tissue 80, as illustrated in FIG. 6, platen 76 will contact the tissue surface and prevent further penetration by needle 62. This ensures that needle 62 may be inserted to a consistent depth at each successive injection site. Also, if the surface of target tissue 80 is curved, platen 76 will press against target tissue 80 and flatten out the curvature, thereby further assuring that needle 62 penetrates to a consistent depth.

Platen 76 includes a raised marking ring 78 on its distal outer side for making a discernable mark on the tissue surface when needle 62 is inserted into the tissue. Marking ring 78 is a raised ring that concentrically encircles needle 62. Ring 78 may be constructed of an absorbent polymeric substance saturated with a visual dye, such as methylene blue. When ring 78 is pressed against tissue, ring 78 will leave a discernable ring-shaped mark on the tissue. The ring-shaped mark will indicate to the surgeon which area of tissue has already receive an injection of therapeutic substance 64. Alternative marking substances for use with the present invention may include contrast agents or fluoroscopic dyes which will allow the use of echocardiographic or fluoroscopic viewing of dye markings and placement patterns.

As illustrated in FIG. 4, syringe 24 may be moved axially forward in the distal direction relative to tubular body 12 to extend needle 22 and platen 76. Syringe 24 is moved forward against the bias of spring 36, thereby compressing spring 36. As syringe 24 is moved distally, flexible tube 60, needle 62 and platen 76 also move distally so that needle 62 and marking ring 78 extend beyond the distal edge 72 of cup 70. Second stop member 40 is fixed on syringe 24 in a location which ensures that when second stop member 40 comes into contact with cap 18, needle 62 and marking ring 78 are properly extended beyond the distal edge 72 of cup 70. Syringe 24 may be retained in the forward position by a latch (not shown), by the surgeon's hand, or by other means. Upon release of syringe 24, spring 36 will force syringe 24 back in the proximal direction, thereby retracting needle 62 and platen 76 back into cup 70. This enables needle 62 to properly retracted following each injection so that needle 62 does not accidentally penetrate non-target areas.

Flexible tube 60 is able to flex in the transverse direction, as illustrated in FIGS. 3–5, but has sufficient column strength so that as syringe 24 is moved forward, flexible tube 60 will push platen 76 and needle 62 distally so that needle 62 is able to penetrate target tissue 80, as illustrated in FIG. 6. Suitable materials for use as flexible tube 60 include hypotube, polyvinyl chloride tube, or other sufficiently stiff biocompatible materials. In addition, to prevent tube 60 from buckling, the clearance between flexible tube 60 and the lumen wall 18 of tubular body 12 may be small enough so that lumen wall 18 will support flexible tube 60.

Figure 7:
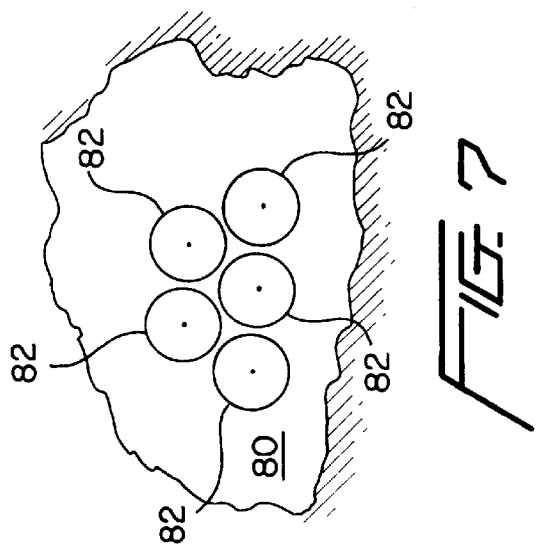
FIG. 7 shows a typical injection pattern for delivery of a therapeutic substance to an area of tissue.

As illustrated in FIG. 6, once needle 62 has penetrated the target tissue 80, marking ring 78 on platen 76 will come into contact with the surface of tissue 80. Then, as illustrated in FIG. 5, plunger thumb button 30 is depressed so that a quantity of therapeutic substance 64 is injected into tissue 80. Plunger stop 31 contacts the proximal end 35 of syringe 24, thereby ensuring that a predetermined dose of therapeutic substance is delivered. Needle 62 is then withdrawn from target tissue 80, and marking ring 78 leaves a discernable mark on target tissue 80. The distal end of device 10 is then repositioned to the next target site for the next injection. In this manner, an area of tissue 80 may be treated with therapeutic substance 64 without overlap. A typical grid-like pattern for such treatment is illustrated in FIG. 7, showing a plurality of ring-shaped marks 82 formed on the surface of tissue 80 by marking ring 78 during successive injections.

When determining the amount of solution to be expelled from needle 62, factors taken into consideration include the proximity of the injection sites to each other and the mobility of the solution within tissue 80. To simplify the process, the area covered by ring 78 is preferably the same as the estimated dispersion area of the predetermined injection quantity of therapeutic substance within the tissue. In addition, the amount of fluid delivered will vary in correspondence with the type of treatment being administered. Accordingly, the spacing of the injection sites, the volume of therapeutic substance to be delivered, the mobility of the therapeutic substance in tissue, the desired area of coverage, and the depth of delivery are all factors which may be taken into account when determining the spacing of the injection pattern. The geometric pattern shown in FIG. 7 provides diffuse coverage with minimal overlap, and with minimal uncovered areas within the overall geometry.

The distance which needle 62 extends beyond platen 76 may be adjusted from patient to patient and for particular uses by using needles of different length. One reason for controlling the depth of needle penetration when treating ischemic heart disease is to ensure that the needle tip is located sub-epicardially, e.g., at approximately 5 mm depth. Platen 76 ensures that the needle tip is always located at the same depth within the tissue during each injection. This ensures a more uniform delivery of the therapeutic substance over the entire treatment area. Of course for some treatment purposes, differing amounts of fluid could be delivered to different areas of tissue by controlling the quantity of fluid dispensed from the syringe during each injection.

Additional features of device 10 may include a fiber optic light source (not shown) located at the distal tip of device 10. The light source may emit from platen 76, from the edge of cup 70, or from other locations. The light source would aid in visualization of the target tissue prior to injection, and also in visual perception of the ring-shaped markings 82 following injection and contact of the target tissue with marking ring 78.

While it will be apparent that the particular dimensions of device 10 may vary for particular applications, the preferred embodiment of device 10 is between 12 and 18 inches in overall length. The maximum diameter of the preferred embodiment is less than 12 mm for the portion of device 10 which is inserted into the patient. This enables device 10 to fit through a 12 or 15 mm thoracoscopic port.

The device of the subject invention may be used to inject a variety of fluids into tissue for a variety of therapeutic reasons. In one preferred method of the present invention, the delivery device is used to deliver an angiogenesis-promoting compound to a portion of the myocardial wall that is suffering from insufficient blood supply. The treatment may be used independently for promoting the growth of new blood vessels, or may be used in conjunction with other procedures such as angioplasty, bypass surgery, transmyocardial revascularization, or the like. The device of the subject invention enables quick, precise, and effective delivery of controlled quantities of the angiogenesis-promoting substance over a desired coverage area with minimal overlap.

Several growth factors have been identified and are intimately involved in initiating and promoting angiogenesis. Included in this family of angiogenic growth factors are acidic fibroblast growth factor ("aFGF"), basic fibroblast growth factor ("bFGF"), and vascular endothelial growth factor ("VEGF"). VEGF in particular has been shown to be capable of promoting angiogenesis in several models of chronic ischemia, including ischemic myocardium in both porcine and canine experiments, and also in the ischemic hind limbs of lab animals.

A preferred method of delivering VEGF is in the form of cDNA or gene coding in a replication-deficient adenoviral ("Ad") vector. A quantity of adenovirus carrying the desired genetic component is delivered to the treatment area by injection in solution. Previous studies have shown the feasibility and efficacy of safe, sustained, and localized expression of VEGF utilizing adenoviral mediated gene transfer therapy.

Thus, under one aspect of the present invention, a predetermined quantity of angiogenesis-promoting factor is loaded into syringe 24, and plunger stop 31 is set at a predetermined distance 33 for dispensing 0.1 cc of the angiogenesis-promoting factor. The patient's heart is accessed via a thoracotomy incision of 7 cm or less, or, in a thoracoscopic approach, via a 15 mm port. Additional ports may be used to provide visualization and manipulation of tissue. A pericardial incision is formed, and stay sutures are emplaced. With the heart appropriately positioned, using retracting devices or the like, cup 76 of device 10 is placed adjacent to the myocardial wall. Needle 62 is then extended to penetrate the target tissue until ring 78 contacts the tissue. Plunger 28 is then depressed until plunger stop 31 contacts the proximal end 35 of syringe 24 to deliver the angiogenesis-promoting factor to the ischemic myocardial tissue in the manner described above. Needle 62 is then withdrawn and repositioned at the next target site. Plunger stop 31 is moved back along plunger rod 26 a predetermined distance 33 for dispensing a second dose of the angiogenesis-promoting substance.

Additional areas of tissue are injected until the entire target area has been treated. A typical procedure may comprise 10 injections of 0.1 cc each for a total of 1.0 cc of angiogenesis-promoting substance being delivered over a 10 $cm^2$ area. Of course, specific amounts of substance delivered, and the area covered will be dictated by the specific treatment being implemented, and the above specifics are not intended to be limiting and are only given for describing the preferred best mode of treatment.

Following injection into the tissue, the angiogenesis-promoting factor initiates the complex process of angiogenesis in the treated tissue, thereby inducing the growth of new blood vessels. This treatment is of benefit to heart tissue in which the existing blood vessels are clogged or narrowed, and is also of benefit to heart tissue which is poorly supplied by the native coronary vasculature for congenital reasons.

Thus, the present invention sets forth a method and apparatus for delivering predetermined quantities of therapeutic substance to biological tissue successively at a plurality locations to achieve therapeutic treatment over a desired area of tissue quickly and accurately. Other uses and benefits of the disclosed present invention will be apparent to those skilled in the art. Therefore, while preferred embodiments of the invention have been described herein, it will be recognized that a variety of changes and modifications may be made without departing from the spirit of the subject invention, the scope of which is set forth in the following claims.

What is claimed is:

1. A device for injecting a therapeutic substance into bodily tissue wherein a portion of the device is inserted into a cavity within a body of a patient prior to injection, said device comprising:

an elongate tubular member having a proximal end for operation outside of the patient's body, and a distal end for operation inside the patient's body;

an elongate flexible tube located within said tubular member, said flexible tube having a proximal end and a distal end, said distal end having a needle mounted theron; and a marking ring mounted on the distal end of said flexible tube for leaving a discernable indication on the bodily tissue at the location where the therapeutic substance is injected, said flexible tube being moveable axially relative to said tubular member for remotely extending and retracting said needle mounted on the distal end of said flexible tube, whereby, when extended, said needle can penetrate the bodily tissue of the patient for injecting the therapeutic substance into the tissue.

2. The device of claim 1 further including a cup mounted on said distal end of said tubular member, said needle and said platen being maintainable in a retracted position in said cup during positioning of said needle within the patient's body relative to the bodily tissue, said needle and said marking means being subsequently extendable from said cup when said needle is intended to penetrate the bodily tissue by moving said flexible tube axially relative to said tubular member.

3. The device of claim 2 further including a control means located on the proximal end of said tubular member and operable to remotely control the attitude of said cup relative to the bodily tissue of the patient within the patient's body.

4. The device of claim 2 further including a syringe for containing the therapeutic substance, said syringe being in fluid communication with said needle through said flexible tube, said syringe also being axially movable relative to said tubular member for extending said needle and said marking ring from said cup.

5. The device of claim 1 further including a platen, said needle projecting from said platen, said platen including said marking ring thereon, said platen being remotely movable with said flexible tube and said needle, whereby, when said needle penetrates the bodily tissue, said marking ring contacts the surface of the bodily tissue for creating a discernable mark thereon, while said platen also limits the depth of penetration by said needle.

6. The device of claim 5 wherein said marking ring includes an absorbent material saturated with a dye.

7. The device of claim 1 further including a control means mounted near said proximal end of said tubular member, said control means being operable outside the body of the patient for remotely causing the distal portion of said tubular member to flex transversely for controllably positioning said needle inside the body of the patient.

8. A device for delivering a therapeutic substance to a bodily tissue, said device comprising:

an elongate tubular member, said tubular member having a proximal end and a distal end;

a flexible tube located within said tubular member, said flexible tube having a proximal end and a distal end;

a hollow needle disposed at said distal end of said flexible tube for delivering the therapeutic substance into the bodily tissue; and a remotely extensible and retractable marking means located on the distal end of said flexible tube, said marking means being capable of indicating when an injection has been made in the tissue.

9. The device of claim 8 wherein said marking means includes a platen, said needle being mounted on said platen, said platen including a marking ring thereon, whereby when said needle penetrates the bodily tissue, said marking ring will contact the surface of the tissue for creating a discernable mark thereon.

10. The device of claim 9 wherein said marking ring includes an absorbent material saturated with a dye.

11. The device of claim 8 further including a cup mounted on said distal end of said tubular member, said needle and said marking means being maintainable in a retracted position in said cup during positioning of said needle relative to the bodily tissue, said needle and said marking means being subsequently extendable from said cup when said needle is intended to penetrate the bodily tissue.

12. The device of claim 11 further including a syringe for containing the therapeutic substance, said syringe being in fluid communication with said needle through said flexible tube, said syringe being movable relative to said tubular member for extending said needle and said marking means.

13. The device of claim 8 further including a control means for enabling said distal end of said tubular member to be controllably flexed in a transverse manner for positioning said distal end of said tubular member proximate to the bodily tissue.

14. A method of delivering a therapeutic substance to an area of bodily tissue within the body of a patient, said method comprising:

provioding an elongate tubular member having a proximal end and a distal end, said tubular member having a needle and a marking means extensible from said distal end;

inserting the distal end of said tubular member into the patient's body;

positioning said distal end of said tubular member proximate to the bodily tissue to be treated;

retaining said needle and said marking means in a retracted position during positioning of said distal end relative to the bodily tissue;

extending said needle and said marking means to penetrate the tissue with said needle;

injecting said therapeutic substance; and marking said tissue to indicate the location of the injection.

15. The method of claim 14 further including the step of repositioning said distal end and said needle proximate to the bodily tissue in a location adjacent to the first injection site for making successive injections.

16. The method of claim 15 wherein the locations for the subsequent injections are determined at least in part based upon marks left at the location of previous injections.

17. The method of claim 14 in which said tubular member is inserted into the patient through a port located within an incision in the patient's body.

18. The method of claim 14 in which a plurality of successive injections are made in a grid-like pattern over an area of tissue, with a mark being left at the site of each successive injection to ensure coverage of the entire desired area of tissue being treated.

19. The method of claim 14 in which the therapeutic substance is retained within a syringe in fluid communication with said needle by a flexible tube, said syringe and said flexible tube being movable axially relative to said tubular member so that said needle is extended by the step of moving said syringe and said flexible tube axially relative to said tubular member.

20. The method of claim 14 wherein a platen is included for contacting the tissue during injection, said platen and said needle being fixed relative to each other, and said marking means comprising a raised ring located on the surface of said platen, whereby, when said needle penetrates the tissue, said marking means and said platen contact the tissue surface for controlling the depth of penetration by said needle.

* * * * *